United States Patent
Stumm et al.

(10) Patent No.: US 7,203,133 B1
(45) Date of Patent: Apr. 10, 2007

(54) ULTRASOUND SENSOR SYSTEM

(75) Inventors: Wolfgang Stumm, Erbach (DE); Volker Arndt, Erbach (DE); Norbert Blumentritt, Michelstadt (DE); Michael Lach, Erkrath (DE); Michael Platte, Wuppertal (DE)

(73) Assignee: Robert Bosch GmbH, Stuttgart (DE)

( * ) Notice: Subject to any disclaimer, the term of this patent is extended or adjusted under 35 U.S.C. 154(b) by 998 days.

(21) Appl. No.: 10/049,088

(22) PCT Filed: Aug. 2, 2000

(86) PCT No.: PCT/DE00/02545

§ 371 (c)(1),
(2), (4) Date: Apr. 29, 2002

(87) PCT Pub. No.: WO01/11353

PCT Pub. Date: Feb. 15, 2001

(30) Foreign Application Priority Data

Aug. 7, 1999 (DE) ................................ 199 37 479

(51) Int. Cl.
*G01N 29/04* (2006.01)
*B23K 11/25* (2006.01)

(52) U.S. Cl. .......................... 367/140; 73/588; 73/597; 219/78.01; 219/109

(58) Field of Classification Search ................ 367/140; 219/78.01, 109; 73/597, 588
See application file for complete search history.

(56) References Cited

U.S. PATENT DOCUMENTS

| | | | | |
|---|---|---|---|---|
| 3,384,733 A | * | 5/1968 | Burbank et al. | 219/109 |
| 4,099,045 A | * | 7/1978 | Okuda et al. | 219/109 |
| 4,208,917 A | * | 6/1980 | Aoyama et al. | 73/644 |
| 5,907,521 A | * | 5/1999 | Matsui et al. | 367/162 |
| 6,297,467 B1 | * | 10/2001 | Maev et al. | 219/109 |

FOREIGN PATENT DOCUMENTS

EP 0 653 061 B1 6/1998

* cited by examiner

*Primary Examiner*—Ian J. Lobo
(74) *Attorney, Agent, or Firm*—Michael J. Striker

(57) ABSTRACT

The invention relates to an ultrasound sensor system, especially for a welding electrode, comprising a sensor (5, 6, 7, 10) which, during the detection process, passes ultrasonic waves of a desired oscillation mode into areas to be detected and/or detects ultrasonic waves. At least one material recess (2) is provided in a sensor support (1), and at least one sensor (5, 6, 7, 10) is arranged in said recess.

18 Claims, 8 Drawing Sheets

Fig. 1a

VIEW A-B 5, 6, 7, 10

ULTRASOUND SENSOR SYSTEM

RELATED ART

The invention is based on an ultrasound sensor system according to the definition of the species in the independent claim.

The evaluation procedure described in EP 653 061 B1 basically comprises the transmission of transverse waves instead of longitudinal waves through the intended welding region during the welding procedure. The amplitude of the through-transmission signal is captured on-line and used as controlled variable for amplitude and variation in time of the welding current. The transverse wave is selected because the influence of fluid formation in the weld nugget on the damping of a through-transmitted wave is very great with this wave mode. The amplitude—which changes markedly and in characteristic fashion over the course of the welding process—or the course of the transverse wave over time provides a reliable conclusion about the formation and size of the weld nugget and can therefore be used as manipulated variable for a control process.

The fundamental feasibility of the procedure and the reliability of the test findings depends decisively on the ultrasound sensors used, their arrangement in terms of the welding electrode, and the sound propagation within the welding electrodes. In the realization according to EP 653 061 B1, ultrasound transmitters and receivers are secured to the external electrode adapter or to the electrode holder. Shear waves, in particular transverse or torsional waves, having a frequency of less than 1 MHz are generated. Cited as a particular advantage is the generation of horizontally polarized transverse waves, because these have a low tendency to undergo undesired mode changes in the case of reverberations within the sound-propagating electrode holder. The ultrasound transmitters and receivers are "shear wave probes". They contain flat and mostly round piezoelectric plates having a diameter of a few mm up to a few cm that make a shearing motion when excited with an electrical voltage or, conversely, during receiving, they react to a received shear wave with a received voltage. To transfer shear waves between probe and solid, they must be in intimate contact with each other. They are usually cemented together. So that the entire sound-sensitive contact surface of the probe becomes effective during sound transmission into the cylindrical electrode adapter, sound-conducting attachments are inserted between probe and electrode adapter, the ends of which are adapted to the surfaces of the probe and to the external contour of the electrode adapter in material-engaging fashion in each case. The horizontal polarization direction, which is advantageous with regard for the tube wall, can be achieved by rotating the probe around its axis or around the axis of its direction of radiation.

It is indicated that an arrangement of the probes perpendicular to the electrode adapter is also possible in cases of low frequencies. The disadvantages that result from radiation in the direction of the inner wall of the electrode instead of in the direction of the welding spot also apply without limitation for transverse waves. Only a small fraction of the acoustic energy is radiated in the desired direction. This also applies in cases of low frequency or a low ratio of diameter of the piezoelectric ply used to the wavelength. Attachments that are preferably designed in the shape of a wedge are used to increase the portion of acoustic energy emitted in the direction of the weld nugget. Sound radiation directed entirely in the direction of the weld spot cannot be achieved with this, however.

Moreover, attaching probes to the side of the electrode adapter is disadvantageous in practice for further reasons. Due to their basic construction out of piezoelectric ply and backward damping element, common commercial shear wave probes have a depth propagation that is usually comparable to their diameter, i.e., a few mm to a few cm. Additionally, due to the damping element, they mainly have a self-weight that is from a few ten grams to a few hundred grams, depending on the size. The damping element is necessary in order to achieve a damped oscillatory behavior of the piezoelectric ply or a broadband frequency transmission behavior. The depth propagation of the probes plus that of the wedge-shaped attachments used leads to a situation in which, in automated production facilities where the welding electrodes are guided by robot arms, the freedom of motion of these robot arms is more or less restricted. When the welding electrodes move, the laterally-attached probes and wedge-shaped attachments act as seismic masses. They are subject to continuously changing forces of acceleration, so that corresponding shear forces are exerted on the connections between electrode adapter, attachments, and probes. When subjected to such alternating stresses, glued joints run the risk of fatigue failures. If a collision with an obstacle occurs, there is also a risk that a probe will be torn off immediately or even destroyed. Such a system is therefore not sufficiently failsafe for long-term industrial use without further mechanical safety devices.

When shear wave probes are attached to the side, the use of attachments to transmit sound into the electrode adapter is absolutely essential. Other fundamental sound-related disadvantages must thereby be accepted, however. The glued joints act in a more or less strongly reverberating fashion between attachments and electrode adapter on the one hand and, on the other hand, between probe and attachment, depending on the ratio of adhesive ply thickness to wavelength, so that, in turn, only a fraction of the acoustic energy passes through the bonding surface, and the ultrasonic signal passing through is also weakened by every further adhesive ply as compared to the original signal. When different materials are used for attachment and electrode adapter, the different acoustic impedances lead to further reverberation losses. Additionally, a sound wave obliquely incident on the border between two adjacent solids is subject to cleavage into through-passing and reverberated longitudinal and transverse waves, the angle of refraction or reverberation of which result from the ratio of sound propagation velocities of the adjacent materials in accordance with the known physical laws for sound refraction. The disadvantages caused by adhesive plies and sound refraction could only be prevented, then, if electrode adapter and attachment would be produced connected out of one material. The production of a part shaped in such complicated fashion would be very costly, however.

The object of the present invention—especially with regard for the named method for the analysis and process control of resistance spot welds—is to provide an improved ultrasound sensor system for welding electrodes with which ultrasonic waves having a desired mode of oscillation, in particular transverse waves such as shear or torsional waves having a frequency of less than 1 MHz, can be transmitted into the sheet-metal regions to be welded during the welding procedure, and with which the pulses of ultrasonic energy reflected by the sheet-metal regions to be welded or passing through them can be detected. It should further be highly sensitive when transmitting or receiving, and it should be easy to manufacture and have small dimensions, so that the freedom of motion of the robot arms guiding the welding electrodes is not impaired. It must also be so robust in construction that it resists the fluctuating forces of acceleration that occur continuously during the positioning, placement, and lifting of the welding electrodes.

ADVANTAGES OF THE INVENTION

The object of the invention is attained by integrating the ultrasound sensor in a sensor carrier, whereby at least one material recess such as a groove is provided to accommodate ultrasound sensors. The ultrasound sensor can be accommodated in protected fashion, making this system suited for industrial use, e.g., using welding robots. Physical size can be reduced by using an arrangement of ultrasound sensors integrated in the sensor carrier, as opposed to arranging them on the side. Additionally, the ultrasound sensors can be more easily attached to the sensor carrier.

These material recesses form flat surfaces preferably in the direction of radiation or detection, which surfaces are positioned either perpendicular to the longitudinal axis of the sensor carrier so the main radiation direction of the ultrasound sensors is parallel to the longitudinal axis of the sensor carrier, or they are tilted toward the longitudinal axis of the sensor carrier in order to create other advantageous sound propagation directions.

In an advantageous further development, the ultrasound sensor comprises, in addition to a piezoelectric ply, at least one sound-damping and/or reverberating ply. This allows sound propagation to be directed in a desired direction, which improves the transmission/receiving power of this system.

A further advantageous embodiment provides an intermediate ply composed of non-piezoelectric material, the acoustic impedance of which nearly corresponds to the material of the sensor carrier or a value that is between sensor material and sensor carrier. This intermediate ply is preferably located between the sensor carrier and the piezoelectric ply generating the ultrasonic waves. This makes it possible to achieve good sound transmission between the piezoelectric element and the sensor carrier. Additionally, this intermediate ply ensures electrical insulation between piezoelectric element and sensor carrier.

In an advantageous further development, means are provided to prevent propagation of ultrasonic waves in a direction that extends radially to the longitudinal axis of the sensor carrier. For example, an intermediate space or a separating ply extends between the ultrasound sensor and the sensor carrier parallel to its longitudinal axis in order to prevent radial propagation of ultrasonic waves. Transmitter power and/or sensitivity of reception can thereby be improved.

An advantageous embodiment provides means for the electrical shielding of the piezoelectric ply in order to reduce perturbing actions.

In a further development, the sensor comprises at least two plies of piezoelectric material having polarization directions that alternate from ply to ply. This system makes it possible to improve the transmitting and/or receiving properties, because greater field intensitys and, accordingly, greater deflections, can therefore be achieved.

The proposed sensor system is particularly suited for use in welding electrodes, but it is not limited to this.

Further advantageous further developments result from the further dependent claims and the description.

BRIEF DESCRIPTION OF THE DRAWING

An exemplary embodiment of the invention is presented in the drawing and is described in greater detail hereinafter.

DETAILED DESCRIPTION OF THE EXEMPLARY EMBODIMENTS

The exemplary embodiments are based on a potential application in welding electrodes. The electrode adapter forms the sensor carrier for at least one ultrasound sensor.

Figure 1A:
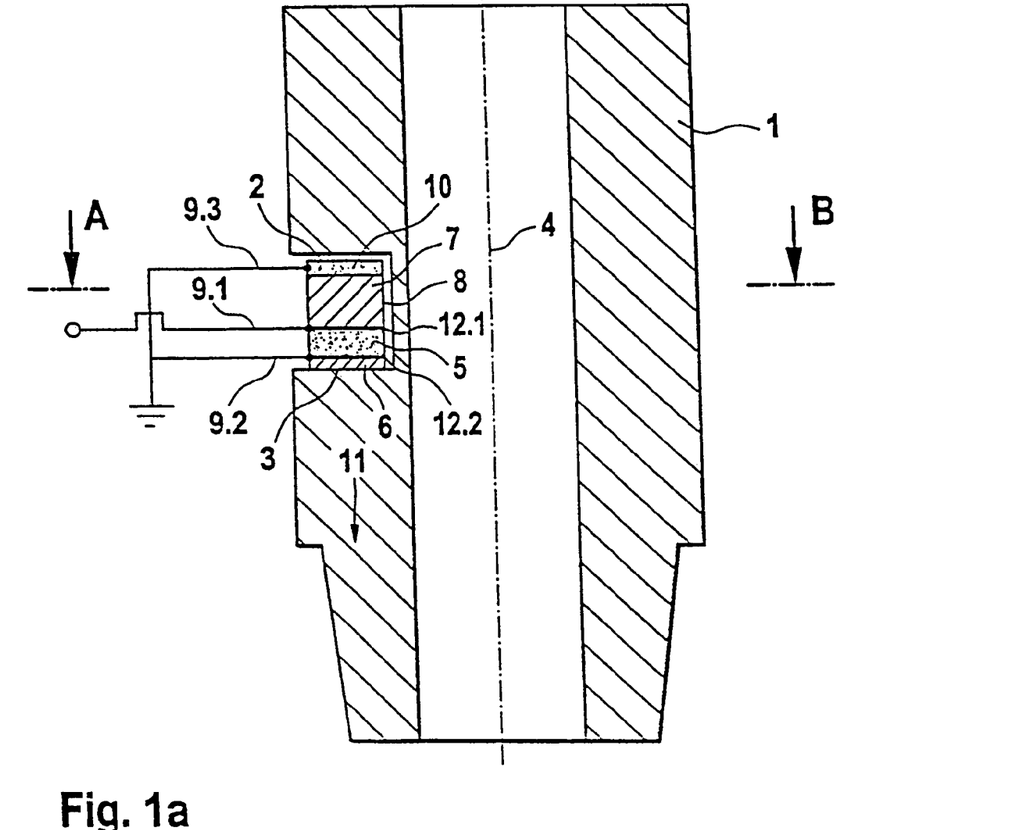
FIGS. 1a–1f show exemplary embodiments of the ultrasound sensor system according to the invention.

FIG. 1a shows the principle mode of operation of the ultrasound sensor system according to the invention using one of the potential exemplary embodiments as an example. For the fundamental mode of operation of the invention, it is irrelevant whether the welding electrodes are bipartite and comprise electrode adapter and cap, or how they are shaped on their back end, in order to be accommodated by a holder. These details will be left unpresented initially in this and the subsequent drawings. A recess 2 designed in the shape of a groove is created in the electrode adapter 1. The side of the groove facing the electrode tip forms a surface 3 that is perpendicular to the longitudinal axis 4 of the electrode adapter 1. A, e.g., rectangular, ply 5 composed of piezoelectric material is located on it. This is outfitted with electrodes on both sides by means of electrically conductive plies 12.1, 12.2, which electrodes are connected to the electrical leads 9.1, 9.2. The piezoelectric ply 5 outfitted with electrodes on both sides is connected to the surface 3—with insertion of an intermediate ply 6—in such a fashion that good sound transmission from the piezoelectric ply 5 into the electrode adapter 1 is ensured. The intermediate ply 6 either performs the function of only providing electrical insulation between piezoelectric ply 5 and the electrode adapter 1. In this case, it is preferable to select a material having similar acoustic impedance as the adjacent piezoelectric material or the alloy used to produce the electrode. Or, the intermediate ply 6 is designed as acoustic transformation ply. In this case, its acoustic impedance and thickness are selected with regard for the ratio of the acoustic impedance of piezoelectric ply and electrode material so that the conditions for acoustic quarter-wave or half-wave transformation are met. In a simplified embodiment, however, the ply 6 can be eliminated entirely. The plies 5, 6 can be applied to the surface 3, e.g., by cementing. The influence of the adhesive plies on the acoustic permeability is minimized by expending such a contact pressure during glueing that the thicknesses of the adhesive layers become much smaller than the wavelength of the sound wave generated by the piezoelectric material A damping and sound-absorbing and/or reverberating ply 7 is applied to the back of the piezoelectric layer in similar fashion. It ensures that no portions of sound enter the electrode adapter 1 from the back of the piezoelectric layer 5 by absorbing these portions or reflecting them back to the front in the direction 11, i.e., in the direction of the electrode cap or tip. A lateral intermediate space 8 or an acoustic separating ply filling it can prevent portions of sound from entering the electrode adapter 1 radially from the lateral edges of the piezoelectric ply 5. In this fashion, all of the ultrasonic energy generated in the piezoelectric ply is successfully radiated in the direction of the electrode tip 1.1, so that the transmitting power of this system is increased considerably as compared to the heretofore-known lateral application of the ultrasound at the external electrode adapter.

Due to the reversibility of the sound paths, the same ratios apply as for reception, so that the system according to the invention in FIG. 1a also has greatly increased sensitivity of reception as compared to the case in which the ultrasonic signal is picked up on the side at the external electrode adapter 1.

The arrangement of the sound-generating, piezoelectric ply 5 inside the electrode adapter 1 perpendicular to its longitudinal axis 4 is also particularly advantageous for the transmission of transverse waves because, when sound radiates parallel to the longitudinal axis 4 of the electrode adapter 1, only one grazing incidence of sound takes place with regard for the outer and inner wall of the electrode adapter 1. According to the physical law for refraction, when a grazing incidence of sound takes place, a longitudinal wave basically cannot cleave due to the higher velocity of propagation of the longitudinal wave compared to the transverse wave. As a result, no energy is removed from the original transverse wave, as would be the case more or less with a zigzag-shaped reverberation if the ultrasound were injected at the external electrode adapter at a smaller angle of incidence.

In order to achieve an electrical shielding of the piezoelectric ply 5, an electrically conductive (shielding) ply 10 connected to ground potential via a lead 9.3 or electrically conductive shielding plates or foils having another shape can be inserted on the back ply 7, for example. The ply 10 and the anterior electrode 12.2 of the piezoelectric ply 5 are thereby preferably connected to common potential.

As to be explained using FIG. 1a, a particularly advantageous embodiment of the sensor system according to the invention can be realized when a piezoelectric material is used, the acoustic impedance of which nearly corresponds to that of the electrode adapter. If, at the same time, the ply 6 is eliminated or is composed of a material having similar acoustic impedance as the electrode material, the transient oscillation and attenuation of the piezoelectric plate is damped in such a fashion that a backward damping element (ply 7) can be eliminated entirely, and the height of the ply stack—comprising the plies 6, 5, 7, and 10—forming the ultrasound sensor can be kept very low. The sensor system can then be used as well in welding robots that, due to spacial restrictions, are outfitted with electrodes comprising very short shafts.

Figure 1B:
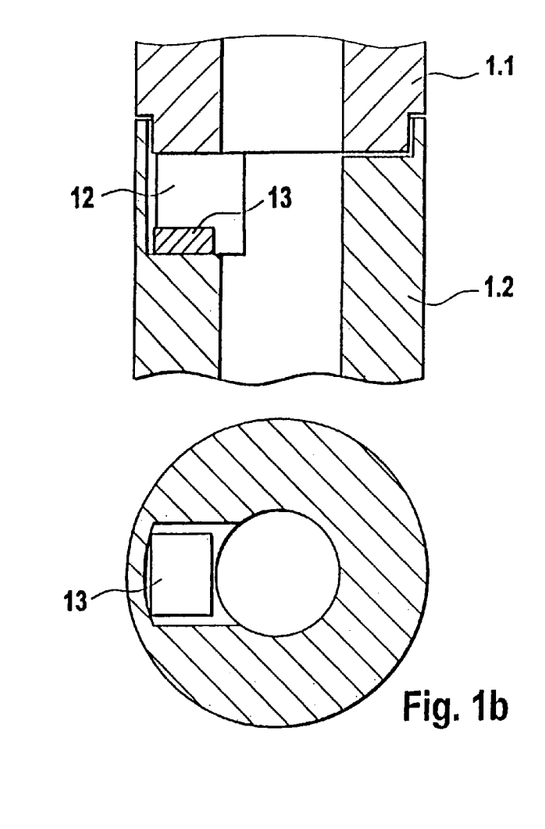

According to FIG. 1b, the groove 12 for accommodating an ultrasound sensor 13 comprising, e.g., piezoelectric ply 5, insulation or transformation ply 6, as well as backward damping or reverberatory ply 7 as in FIG. 1a, can also be applied to the inside of the electrode adapter 1. In this case, the electrical leads must be passed through the wall of the electrode adapter or through the inner cooling hole. The production of the inner grove is simplified when the electrode adapter is first produced in two parts 1.1 and 1.2, which are later fused in material-engaging fashion, e.g., by means of a thread, so that the transition resistance with regard for the welding current remains low.

Figure 1C:
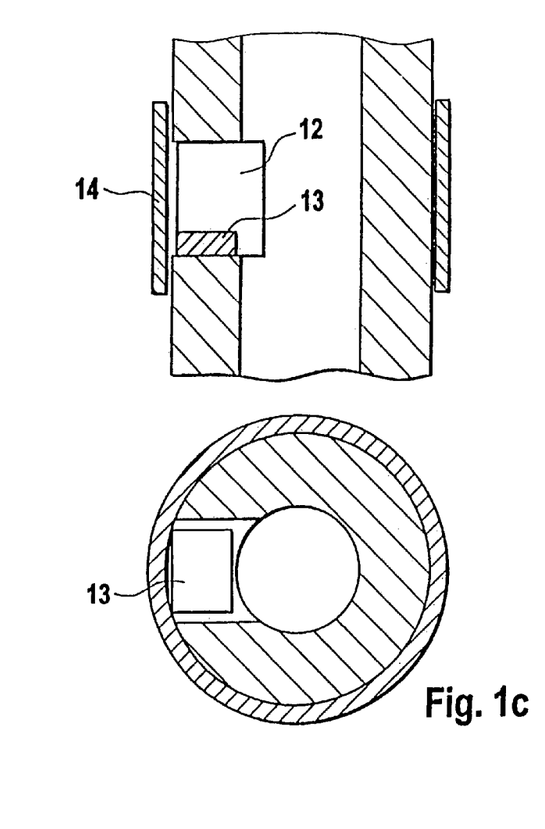

According to FIG. 1c, the groove 12 can also be formed as opening from the inside to the outer wall of the electrode adapter. In this case, the groove must be sealed, e.g., by means of a lateral sleeve 14 made of plastic, to prevent cooling water from escaping from the cooling hole.

Figure 1D:
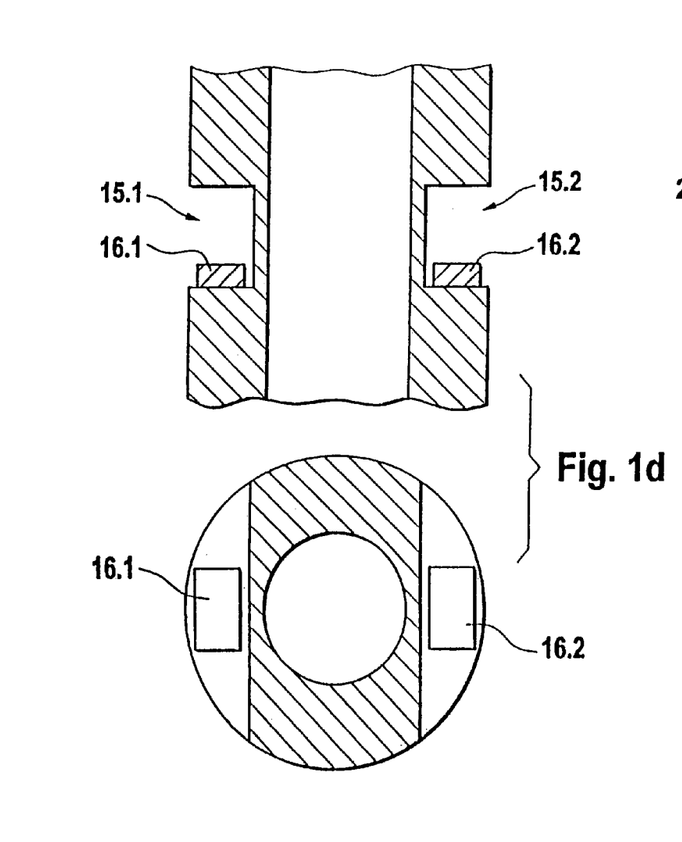

In a further advantageous embodiment of the ultrasound sensor system, according to the invention, not just one groove is created in the electrode adapter 1 to accommodate a piezoelectric ply or a sensor, as shown in FIGS. 1a–c, but two, e.g., diametrally opposed grooves 15.1, 15.2, as shown in FIG. 1d, or further grooves as well that are distributed around the circumference. Every groove itself serves to accommodate a piezoelectric ply, e.g., an ultrasound sensor (16.1, 16.2 in FIG. 1d). All individual sensors formed in this fashion are connected electrically in parallel and actuated isochronically, so they act like a single integrated sensor. As a result, the ultrasound output released in the electrode adapter is increased in proportion to the radiating surfaces, so that the intensity acting in the region of the weld nugget is increased to the same extent, and an improved ratio of useful to interference signals occurs.

Figures 1E, 1F:
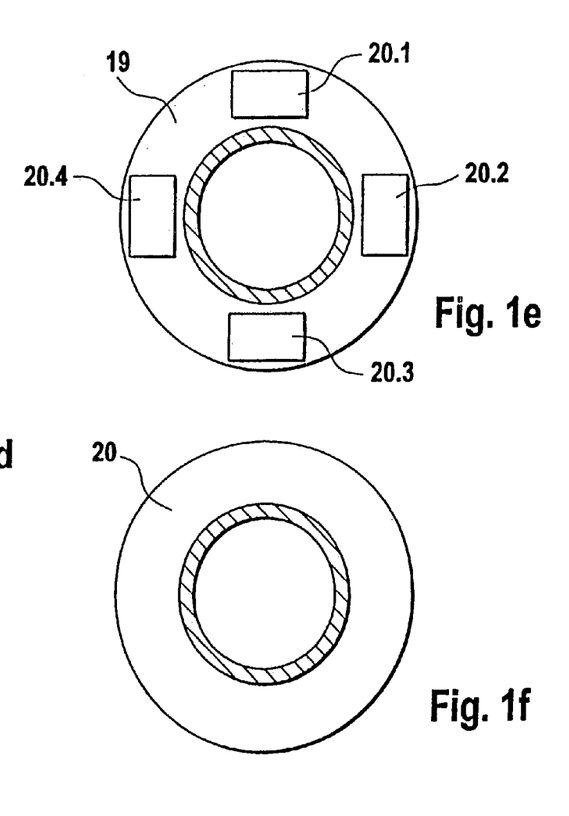

In a further embodiment of the invention, the groove can be designed, according to FIG. 1a, in the shape of a ring around the entire circumference of the electrode adapter, and the annular surface 19 created as a result can be outfitted with a larger number of, e.g., rectangular piezoelectric plies 20.$n$ ($n$=1, 2 . . . N). FIG. 1e shows this for the case N=4. It can also be advantageous, as shown in FIG. 1f, to outfit the entire surface 19 of the annular groove with piezoelectric material and use it as radiating surface. Additionally, corresponding rings 20 or ring segments combinable into rings composed of piezoelectric material can be glued to the surface 19.

The sensor systems according to FIGS. 1d, 1e, and 1f can logically be designed with internal grooves as well. All potential embodiments of the groove for accommodation of the piezoelectric plies are based on the condition that the remaining smallest cross-section of the electrode adapter with its resultantly increased electrical resistance does not hinder the electrical current flow to the extent that, e.g., a strong warming of the electrode adapter occurs, or that the current source cannot provide the desired current flow.

Figure 2:
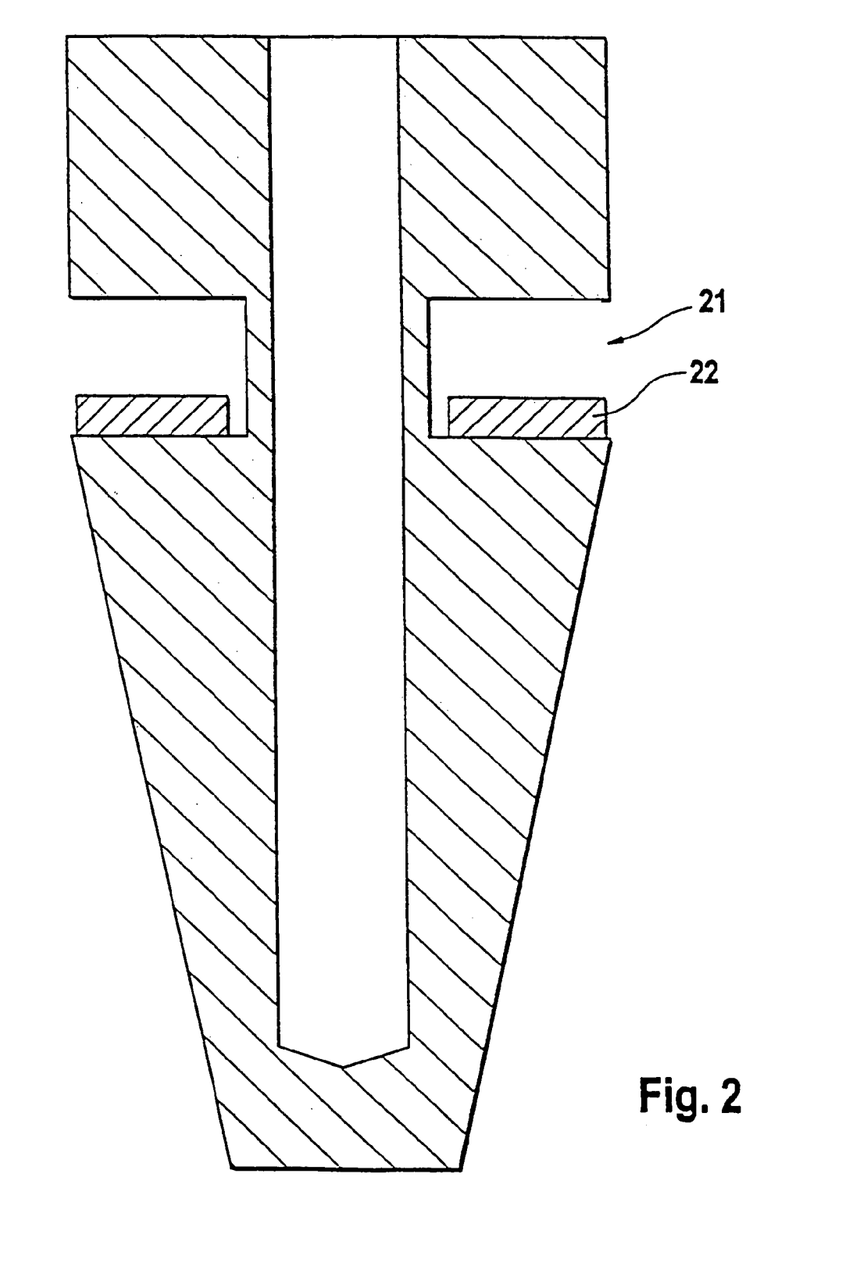
FIG. 2 shows an exemplary embodiment of the ultrasound sensor system according to the invention having an electrode adapter tapering in the direction of the electrode tip.

In a further advantageous embodiment of the invention according to FIG. 2, the greatest possible external diameter is first selected in the upper region of the electrode adapter. Starting at the groove 21 for accommodation of the piezoelectric ply (or plies) 22, the electrode adapter tapers downward in the direction of the electrode tip. The outer diameter of the adapter can decrease, e.g., linearly or exponentially, as the distance from the groove increases. The contour of the lower part then has a conical shape or the shape of an exponential horn. It is particularly advantageous here that the surface of the piezoelectric ply (or plies) 22 is great compared to a uniformly thin electrode adapter and, in turn, the ultrasound output generated or the ultrasonic intensity acting in the region of the weld nugget increases in proportion to the surface of the effective piezoelectric ply 22, while the freedom of motion during positioning of the welding electrodes is retained by means of the downward tapering of the electrode adapter.

Figure 3:
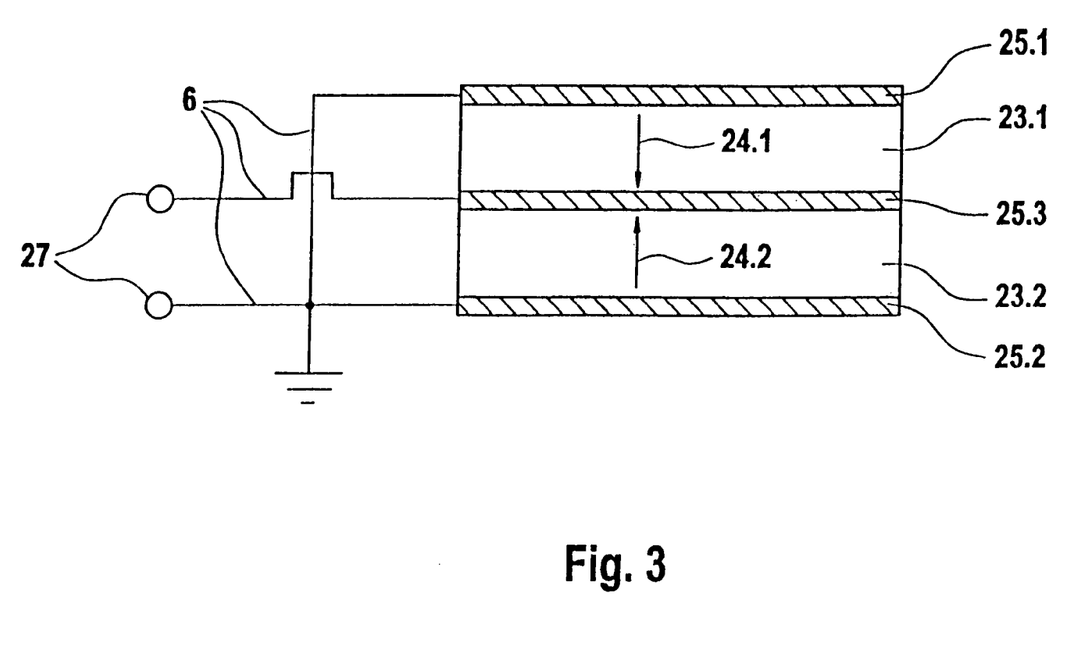
FIG. 3 shows the basic layout of an exemplary embodiment of the ultrasound sensor used in the ultrasound sensor system using stacking technique.
Figure 4:
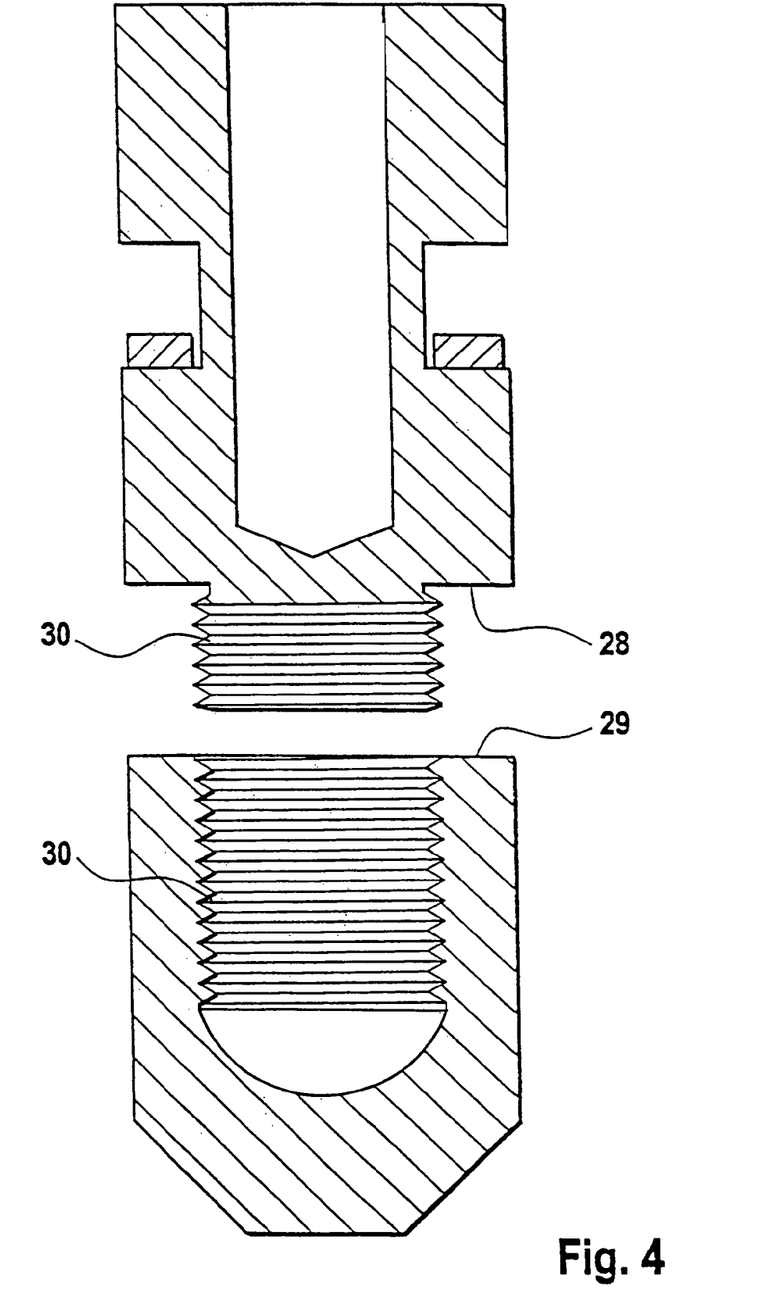
FIG. 4 shows an exemplary embodiment of a welding electrode comprising an electrode adapter and electrode cap that is sonically favorable with regard for the ultrasound sensor system according to the invention.

Further embodiments of the ultrasound sensor system according to the invention also serve to increase the sensitivity of transmission or reception. For instance, the piezoelectric plies or sensors accommodated in the material recesses in the electrode adapter can be designed in a stacked formation, or they can comprise a plurality of plies of piezoelectric material that are stacked on top of each other in alignment and are acoustically connected to each other. FIG. 3 shows this using the example of two piezoelectric plies 23.1, 23.2 having the thickness d. By means of the electrodes 25.1, 25.2, and 25.3 applied across the surface, the piezoelectric elements 23.1, 23.2 form two electrical capacitors that are connected electrically in parallel via the electrical leads 26. The polarization directions 24.1, 24.2 of the piezoelectric elements 23.1, 23.2 point in opposite directions, however. For this reason, the stack comprising piezoelectric elements 23.1 and 23.2 oscillates when an electrical voltage is applied at the terminal 27 like a piezoelectric element having the thickness D=2d. In contrast, however, a field intensity E=U/d is generated in every piezoelectric element in the stack, which field intensity is twice as great as when the same voltage is applied at a single piezoelectric element having a thickness D=2d, so that the acoustic pressure generated is also twice as great. The external electrodes 25.1 and 25.2 thereby simultaneously act as electrical shield. Finally, to improve the sound transmission from the electrode adapter to the electrode cap, the electrode adapter can comprise a shoulder 28 on its lower end extending across a surface that, when the electrode cap is attached, forms a material-engaging and, therefore, sound-permeable contact surface with a shoulder 29 on the electrode cap that is designed to extend across a surface in corresponding fashion. The electrode cap and electrode adapter are advantageously each provided with a screw thread 30 as well, so that both surfaces 28, 29 can be placed under high pretension. As a result, a contact is achieved that remains constant in terms of the surfaces touching in material-engaging fashion and that is favorable in terms of permeability to ultrasound.

Figure 5:
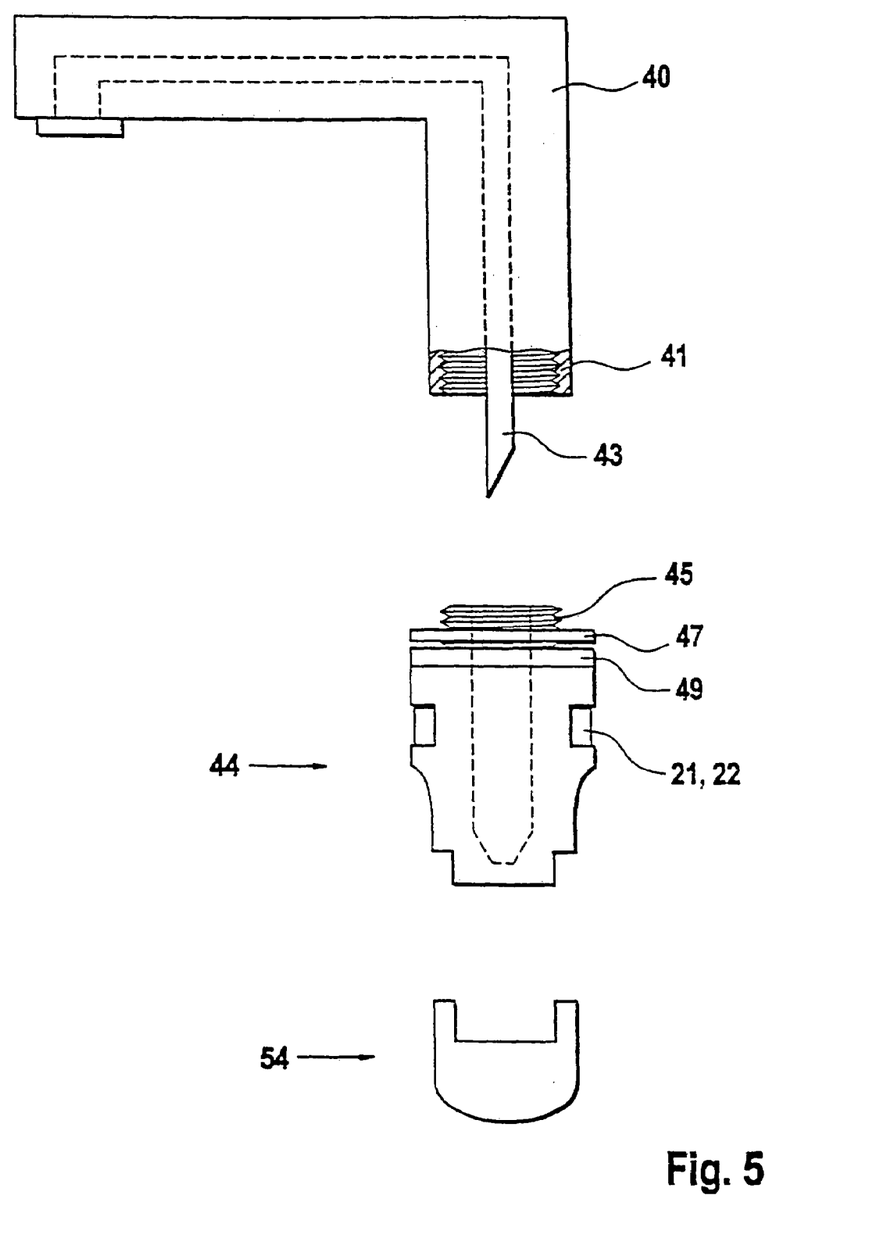
FIG. 5 shows a variant of an ultrasound sensor system integrated in the electrode adapter.

In the exemplary embodiment according to FIG. 5, a cooling tube 43 is directed inside an electrode arm 40. An internal thread 41 is provided on the end of the electrode arm 40 to connect the electrode arm 40 with the electrode adapter 44 that is screwed onto an external thread 45 of the electrode adapter 44. A sealing ring 47 is located between the external thread 45 and a key flange 49 of the electrode adapter 44. Ultrasound sensors 22 are integrated in material recesses 21 in the electrode adapter 44, as described in detail hereinabove. An electrode cap 54 can be placed on the electrode adapter 44.

Figure 6:
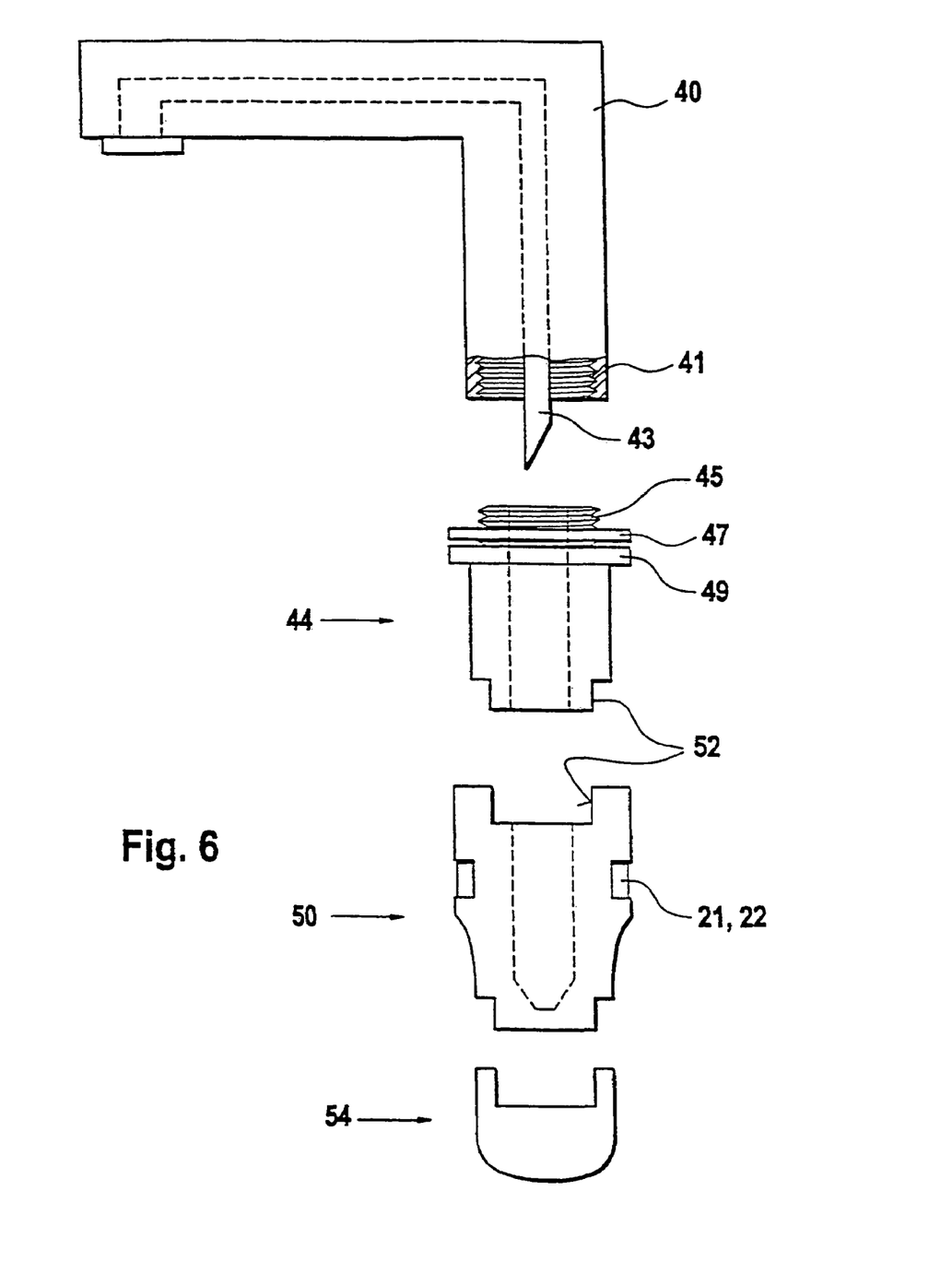
FIG. 6 shows a variant of an ultrasound sensor system integrated in an intermediate part.

The exemplary embodiment according to FIG. 6 differs from that according to FIG. 5 in particular in that an additional intermediate piece 50 is provided with material recesses in which the ultrasound sensors 22 are located. The connection of the electrode adapter 44 to the intermediate piece 50 takes place via a conical fit 52.

What is claimed is:

1. An ultrasound sensor and sensor carrier system for use with a liquid cooled welding electrode in a resistance welding system, the sensor carrier being provided with a cooling bore for carrying liquid coolant to and from the tip of the welding electrode, comprising at least one sensor (5, 6, 7, 10) that transmits ultrasonic waves of a desired mode of oscillation during the detection procedure into regions to be detected and/or that detects the ultrasonic waves, wherein at least one material recess (2) is provided in a sensor carrier (1), whereby the position of the at least one recess is radially offset from a longitudinal axis of the cooling bore and is outside of the cooling bore, and wherein at least one sensor (5, 6, 7, 10) is mounted in the at least one recess.

2. The ultrasound sensor system according to claim 1, wherein at least one surface (3) formed by the at least one material recess (2) is situated perpendicular to the longitudinal axis (4) of the sensor carrier (1).

3. The ultrasound sensor system according to claim 1, wherein at least one plate, washer, ring, or segment composed of piezoelectric material is used as the sensor (5, 6, 7, 10).

4. The ultrasound sensor system according to claim 1, wherein the sensor (5, 6, 7, 10) comprises at least one silencing and/or reverberating ply (7).

5. The ultrasound sensor system according to claim 1, wherein the sensor (5, 6, 7, 10) comprises a ply (6) composed of piezoelectric material, the acoustic impedance of which nearly corresponds to the material of the sensor carrier (1).

6. The ultrasound sensor system according to claim 1, wherein means (8) are provided to prevent a propagation of ultrasonic waves in a direction extending radially to the longitudinal axis (4) of the sensor carrier (1).

7. The ultrasound sensor system according to claim 1, wherein means (10) are provided for the electrical shielding of the piezoelectric ply (5).

8. The ultrasound sensor system according to claim 1, wherein the sensor (5, 6, 7, 10) comprises at least two plies (23.1, 23.2) composed of piezoelectric material.

9. The ultrasound sensor system according to claim 8, wherein the at least two plies (23.2, 23.2) composed of piezoelectric material have polarization directions (24.1, 24.2) that are opposed in alternating fashion from ply to ply.

10. The ultrasound sensor system according to claim 8, wherein the at least two plies (23.1, 23.2) composed of piezoelectric material are electrically connected in parallel.

11. The ultrasound sensor system according to claim 8, wherein the number of plies (23.1, 23.2) is 2n, wherein n is a whole number, and/or the outer ply/plies in each case is/are situated at frame potential.

12. The ultrasound sensor system according to claim 1, wherein the sensor (5, 6, 7, 10) comprises an intermediate ply (6) located between the piezoelectric ply (5) and the surface located in the sensor carrier (1) that is electrically insulating but sound-conductive.

13. The ultrasound sensor system according to claim 1, wherein the sensor carrier is an electrode adapter (1).

14. The ultrasound sensor system according to claim 13, wherein the external electrode adapter (1) tapers in the direction of the electrode tip.

15. The ultrasound sensor system according to claim 13, wherein the electrode adapter (1) comprises a shoulder on its lower end extending across a surface that, when the electrode cap is attached, forms a material-engaging and sound-permeable contact surface with a region of the electrode cap that is designed to extend across a surface in corresponding fashion.

16. The ultrasound sensor system according to claim 1, wherein the sensor (5, 6, 7, 10) generates and/or detects transverse waves.

17. The ultrasound sensor system according to claim 16, wherein the transverse waves are shear or torsional waves.

18. The ultrasound sensor system according to claim 1, wherein waves having a frequency of less than 1 MHz are generated.

* * * * *